US 6,637,273 B2

(12) United States Patent
Okada

(10) Patent No.: US 6,637,273 B2
(45) Date of Patent: Oct. 28, 2003

(54) METHODS AND APPARATUS FOR MEASURING STRESS OF MEMBRANE REGIONS OF SEGMENTED MICROLITHOGRAPHIC MASK BLANKS

(75) Inventor: Masashi Okada, Ibaraki (JP)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 09/998,540

(22) Filed: Nov. 29, 2001

(65) Prior Publication Data

US 2002/0112544 A1 Aug. 22, 2002

(30) Foreign Application Priority Data

Dec. 22, 2000 (JP) ........................................ 2000-389822

(51) Int. Cl.[7] .............................. G01L 15/00; G01L 5/00
(52) U.S. Cl. ............................... 73/716; 378/34; 378/35
(58) Field of Search .............................. 430/22, 30, 5; 378/34, 35, 205, 207; 73/716

(56) References Cited

U.S. PATENT DOCUMENTS 5,983,727 A * 11/1999 Wellman et al. .............. 73/724
6,265,696 B1 * 7/2001 Sakurai et al. ............... 219/390

* cited by examiner

*Primary Examiner*—Eward Lefkowitz
*Assistant Examiner*—Jermaine Jenkins
(74) *Attorney, Agent, or Firm*—Klarquist Sparkman LLP

(57) ABSTRACT

Methods and apparatus are disclosed for accurately measuring stresses in respective membrane regions of segmented mask blanks destined to be made into masks or reticles for use in microlithography. A mask blank is held to a securing plate, e.g., by electrostatic attraction. The mask blank is held such that the struts of the mask blank contact the surface of the securing plate. The securing plate defines an array of through holes that are aligned with individual subfields of the mask blank. A pressure differential is applied across the membrane via the through-holes, causing the membrane regions to bulge. While measuring the pressure, the magnitude of bulge of individual membrane regions is measured using a displacement-measuring device. From data concerning the magnitude of bulge, membrane stress and Young's modulus are determined.

9 Claims, 2 Drawing Sheets

METHODS AND APPARATUS FOR MEASURING STRESS OF MEMBRANE REGIONS OF SEGMENTED MICROLITHOGRAPHIC MASK BLANKS

FIELD

This disclosure pertains to reticles and masks as used in microlithography, especially reticles and masks as used in charged-particle-beam microlithography. More specifically, the disclosure pertains to "mask blanks" from which actual pattern-defining reticles and masks are made, and to methods and apparatus for measuring internal stresses of membrane regions of segmented mask blanks and the like having multiple membrane regions.

BACKGROUND

In recent years, miniaturization of active circuit elements in various microelectronic devices has proceeded at a rapid pace. This development of progressively smaller circuit elements has required the parallel development of ever more sophisticated apparatus and methods for manufacturing microelectronic devices including such circuit elements.

Progress in microelectronic-device-fabrication technology is exemplified by progress in microlithographic exposure technology, by which circuit patterns are imprinted on any of various "substrates" (typically a semiconductor wafer). As the limitations of optical microlithography have been increasingly apparent, considerable attention has been devoted to producing a practical "next generation" microlithography technology. Most of this effort has focused on the use of a charged particle beam (e.g., electron beam or ion beam) or a "soft X-ray" beam. In either of these approaches, the microlithographic pattern to be transferred to the wafer or other substrate is defined on a "reticle" or "mask" that is usually segmented to include multiple membranous regions that define respective portions of the pattern. (In this disclosure, the terms "mask" and "reticle" are used interchangeably; usually the term "mask" is used.)

In a conventional method for fabricating a mask, semiconductor-processing technology is used. The method begins with a silicon substrate as a starting material, from which a "mask blank" (mask that does not yet define a desired pattern) is produced. A representative segmented mask blank 30 is shown in FIGS. 3(a)–3(b), wherein FIG. 3(a) is a plan view and FIG. 3(b) is an enlarged elevational section. As shown in FIG. 3(b), the mask blank 30 comprises a base material 31 (typically silicon), a plurality of struts 32 (typically made of the same material as the base material 31), and at least one thin-film membrane 33 supported by the base material 31 and struts 32. Note that the struts 32 divide the mask blank 30 into multiple "subfields" characteristic of a segmented mask blank, wherein the membrane 33 extends over each subfield between the struts. When the mask blank 30 is made into an actual mask, the membrane region of each subfield is configured with a respective portion of a desired mask pattern. The mask pattern usually is of a circuit pattern to be imprinted as a respective layer on a lithographic substrate.

Referring further to the mask blank 30, whenever the residual stress of the membrane 33 is excessive, pattern distortion occurs after the mask blank is made into a mask. Hence, it usually is necessary to ascertain the magnitude of residual stress in the membrane 33 before or during manufacture of a mask from the mask blank.

Conventional methods for measuring stress and Young's modulus in a membrane include so-called "bulge" techniques. Bulge techniques are advantageous because they can provide stress measurements without damaging the membrane. An overview of a bulge technique is shown in FIG. 4. The depicted bulge technique involves mechanically securing the peripheral portions of a membrane 42 using a membrane-holding plate 44. The membrane 42 is placed over an opening in a pressurization chamber 41. While varying the pressure applied via the chamber 41 to the membrane 42, the magnitude and direction of membrane bulge is measured using a bulge-measuring device 43. From the bulge measurements and from corresponding pressure values, the membrane stress and the Young's modulus of the membrane 42 are determined.

The relationship between pressure applied to the membrane 42 and magnitude of bulging of the membrane 42 can be expressed as in Equation (1):

$$P \cdot [r^2/(d \cdot h)] = K_1 \cdot \sigma + K_2 \cdot [E/(1-\gamma)] \cdot (h/r)^2 \quad (1)$$

wherein P is the pressure applied to the membrane 42, σ is the stress of the membrane 42, E is Young's modulus, γ is Poisson's ratio, r is the membrane radius (if the membrane 42 is circular) or one-half the length of one side (if the membrane is square), d is the thickness of the membrane 42, h is the bulge of the membrane, and $K_1$ and $K_2$ are constants determined according to the shape of the membrane 42.

Thus, using conventional bulge techniques it is possible to measure the stress of the membrane of a mask blank so long as the peripheral portions of the membrane are adequately secured for making the measurements. Unfortunately, however, masks used in actual charged-particle-beam and soft X-ray microlithographic exposure apparatus are segmented and thus have multiple subfields. Each subfield has a respective membrane supported by flanking struts on a support substrate. With such a mask blank it is necessary to control and secure the peripheral portion of an individual subfield membrane in order to perform the measurements. Conventional methods and apparatus simply do not provide the requisite level of control and security for obtaining measurements at the required accuracy.

Furthermore, in an actual segmented mask blank, the center-to-center distance between adjacent subfield membranes is very small (e.g., about 1 mm), and the width of individual struts is even smaller, typically several hundred μm. Such a mask blank is too weak to withstand mechanical clamping. I.e., it is extremely difficult to hold and secure the mask blank securely without causing damage. Another problem with conventional methods and apparatus (in which the periphery of the mask blank is clamped) is that application of pressure to the mask blank causes the entire unclamped region of the mask blank to bulge, which tends to fracture the membranes.

Therefore, obtaining accurate measurements of stress in the membranes of mask blanks (especially segmented mask blanks) currently is extremely difficult.

SUMMARY

In view of the difficulties with conventional techniques for measuring residual stress in the membrane of a mask blank, the present invention provides, inter alia, methods and apparatus for more accurately measuring membrane stress, especially of a segmented mask blank having a plurality of membranous subfields such as would be used to fabricate a mask for use in charged-particle-beam or soft X-ray microlithography.

According to a first aspect of the invention, methods are provided for measuring stress in membrane regions of a segmented mask blank defining multiple subfields each having a respective membrane region flanked by struts that separate the subfields from one another. In an embodiment of such a method, the mask blank is mounted on a securing plate such that the struts contact the securing plate. The securing plate defines an array of through-holes, wherein the array has a pitch substantially equal to the pitch of subfields of the mask blank. The mask blank is situated on the securing plate such that the through-holes are aligned with individual respective subfields of the mask blank. A differential pressure is applied across the respective membrane regions of subfields aligned with respective through-holes. Respective displacements of the membrane regions to which the differential pressure is being applied are measured. From the respective displacements, respective values of membrane stress of the membrane regions are determined based on a relationship between the pressure and magnitude of membrane displacement.

The differential pressure can be applied in a manner that causes bulging of the membrane regions, or that causes indentation of the membrane regions.

The relationship between pressure and membrane displacement can be as expressed above in Equation (1).

Because the struts of the mask blank are held to the securing plate by electrostatic force rather than mechanical clamping, it now is possible to secure the respective periphery of each of multiple subfields firmly, regardless of the distance between adjacent struts or of the weakness of the mask blank. Also, the individual through-holes in the securing plate allow pressure to be applied selectively to respective membrane regions of individual subfields. As a result, it now is possible to measure stress in the membrane regions of individual subfields without such measurements being influenced by measurements obtained at other subfields.

According to another aspect of the invention, apparatus are provided for measuring stress in membrane regions of a segmented mask blank defining multiple subfields each having a respective membrane region flanked by struts that separate the subfields from one another. An embodiment of such an apparatus comprises a securing plate defining an array of through-holes, wherein the array has a pitch substantially equal to the pitch of subfields of the mask blank. As noted above, the securing plate is configured for placing the mask blank thereon such that the struts contact the securing plate and the through-holes are aligned with individual respective subfields of the mask blank. The apparatus also includes a means for holding the mask blank to the securing plate. (In embodiments in which the mask blank is held electrostatically to the securing plate, this means can include a power supply connected at least to the securing plate and configured to generate an electrostatic force sufficient to attract the mask blank to the securing plate.) The apparatus also includes a mechanism for applying a differential pressure across the respective membrane regions of subfields aligned with respective through-holes. The apparatus also includes a device for measuring respective displacements of the membrane regions to which the differential pressure is being applied.

The mechanism for applying a differential pressure desirably comprises a chamber and a device, connected to the pressurizing chamber, configured for creating a pressure inside the chamber relative to outside the chamber, the chamber defining an opening. In this configuration, the securing plate extends across the opening in the chamber.

The device for measuring respective displacements can be one or more of the following: (1) an instrument that employs a stylus-type displacement gauge, (2) an instrument that observes the membrane using a microscope for determining changes in focal position of various loci (e.g., center versus periphery) on the membrane, (3) an instrument that irradiates a light onto the membrane and measures membrane displacement by measuring changes in interference fringes of light reflected from the membrane versus from a reference surface, and (4) an instrument that irradiates a light onto the membrane and measures displacement of a position of light reflected from the membrane.

The foregoing and additional features and advantages of the invention will be more readily apparent from the following detailed description, which proceeds with reference to the accompanying drawings.

DETAILED DESCRIPTION

The invention is described below in the context of a representative embodiment, which is not intended to be limiting in any way.

Figure 1:
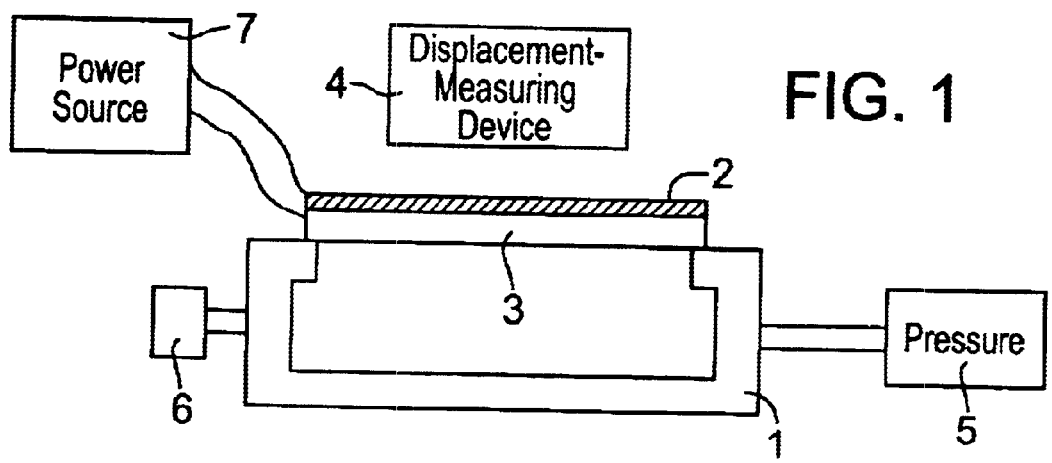
FIG. 1 is a block diagram of a representative embodiment of an apparatus for measuring stress in the membrane of a segmented mask blank.

Reference is made to FIGS. 1 and 2, wherein FIG. 1 is a schematic block diagram of an apparatus, according to this embodiment, for measuring membrane stress in a mask blank (especially a segmented mask blank). The apparatus of FIG. 1 includes a pressurization chamber 1 defining an opening. A mask-blank-securing plate 3 is situated over the opening, and a mask blank 2 is placed on the securing plate 3. Situated over the mask blank 2 is a device 4 for measuring membrane displacement. The chamber 1 is pressurized to a desired pressure using a pressurization means 5 connected to the chamber 1. The chamber pressure is monitored using a pressure gauge 6 (that desirably feeds pressure data back to the pressurization means 5, which controllably responds to the data). The mask blank 2 can be secured to the securing plate 3 by electrostatic attraction, achieved using a suitable power source 7 connected to the mask blank 2 and the securing plate 3.

Figure 2A:
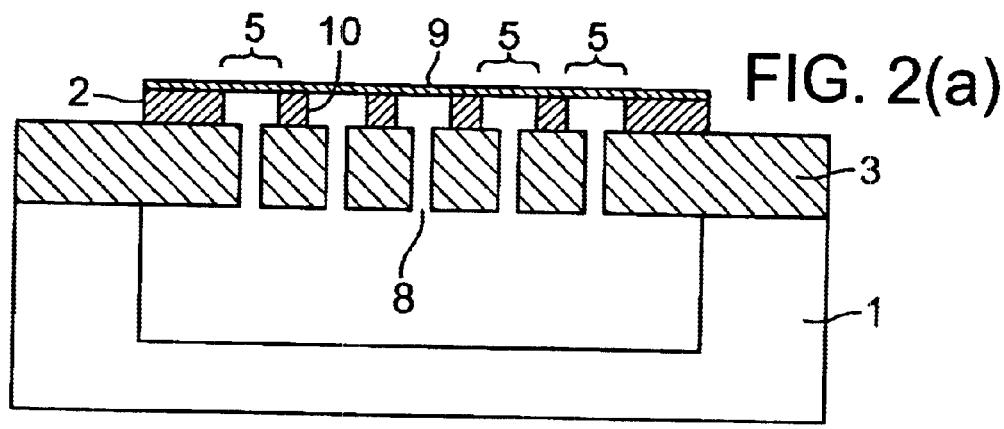
FIG. 2(a) is an enlarged view (viewed as an elevational section) of exemplary peripheral portions of a segmented mask blank as secured by the securing plate of the apparatus of FIG. 1.
Figure 2B:
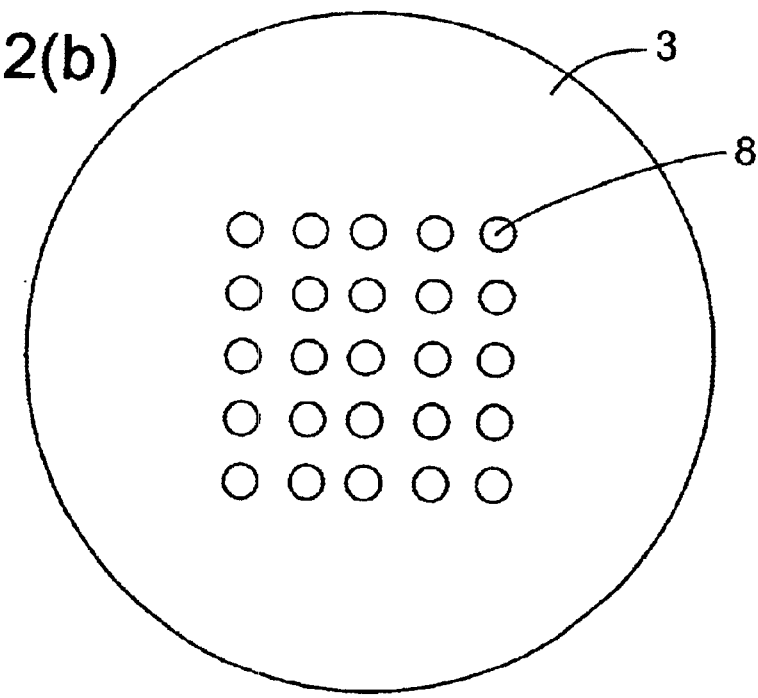
FIG. 2(b) is a plan view of the securing plate of the apparatus of FIG. 1.
Figure 3A:
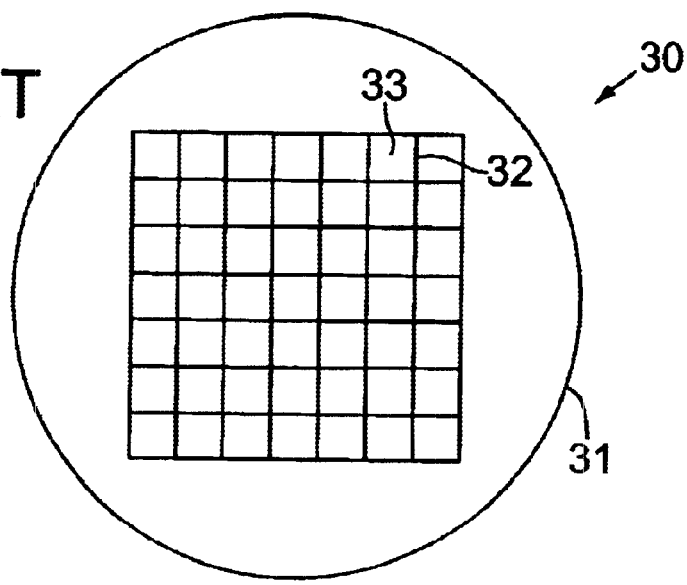
FIG. 3(a) is a schematic plan view of a conventional segmented mask blank.
Figure 3B:
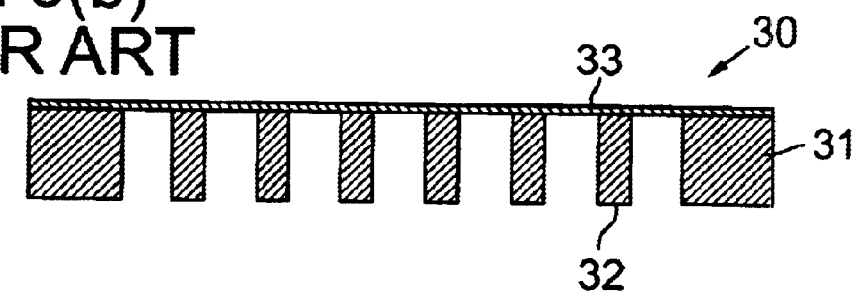
FIG. 3(b) is an elevational section of the mask blank of FIG. 3(a).
Figure 4:
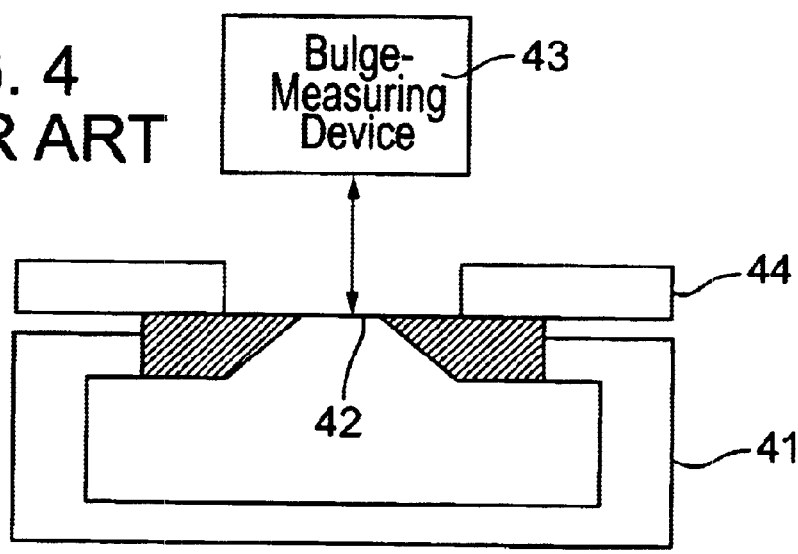
FIG. 4 schematically depicts certain aspects of a conventional bulge technique for measuring membrane stress.

FIG. 2(a) provides an enlargement (viewed as an elevational section) of an exemplary mask blank 2 mounted on the securing plate 3. A plan view of the securing plate 3 is shown in FIG. 2(b). In FIG. 2(a), components that are similar to corresponding components shown in FIG. 1 have the same reference numerals and are not described further. The securing plate 3 defines multiple through-holes 8. The mask blank 2 is placed on the securing plate 3 such that the struts 10 are aligned with the spaces between adjacent through-holes in the securing plate. Thus, each through-hole 8 has access to a respective subfield S (each having a respective portion of the membrane 9). This alignment is possible because the pattern of through-holes 8 on the securing plate has the same pitch as the subfields S on the mask blank 2.

As noted above, the mask blank 2 can be held electrostatically to the securing plate 3. Whenever a voltage is applied to the securing plate 3 and mask blank 2 using the power source 7, an attractive electrostatic force is generated between the securing plate 3 and the struts 10 of the mask blank 2. Thus, the struts 10 of the mask blank 2 are attracted to the securing plate 3 by the electrostatic force. After securing the mask blank 2 in this manner, pressure can be applied by the pressurization means 5 to the pressurization chamber 1. Specifically, the pressure inside the chamber 1 is increased relative to ambient pressure outside the chamber 1. The pressure extends through the through-holes 8 to the respective subfield membranes 9, causing the membranes 9 to bulge (upward in the figure). While measuring the pressure within the pressurization chamber 1 using the pressure gauge 6, the magnitude of bulging of a selected subfield membrane 9 is measured using the measuring means 4.

While measuring the bulge of the membrane at different pressures within the chamber, respective values of membrane stress and Young's modulus are obtained using Equation (1). In a similar manner, respective values of stress and Young's modulus of the other subfield membranes 9 on the mask blank 2 are measured. To measure the other subfield membranes, the position of the securing plate 3 (with mask blank 2 secured thereto) relative to the pressurization chamber 1 can be changed as required. By attracting the struts 10 of the mask blank 2 to the securing plate 3 by electrostatic force, the conventional problem in which the struts 10 tend to rise whenever pressure is applied is eliminated, thereby eliminating deformation of the mask blank 2 during the measurements.

In other words, apparatus and methods according to the invention impart bulging only to the subfield membranes 9 as desired, not to the struts 10 or other portions of the mask blank 2. Hence, it now is possible to measure stress and Young's modulus of individual membrane regions 9 accurately.

By way of example, if the securing plate 3 is made of a rigid material such as ceramic, the voltage necessary to achieve satisfactory electrostatic attraction of the mask blank 2 to the securing plate 3 is about 1 kV.

The displacement-measuring means 4 can be any of various instruments currently available. These instruments include those that: (1) employ a stylus-type displacement gauge, (2) observe the membrane using a microscope for determining changes in focal position of various loci (e.g., center versus periphery) on the membrane, (3) irradiate a light onto the membrane and measure membrane displacement by measuring changes in interference fringes of light reflected from the membrane versus from a reference surface, and (4) irradiate a light onto the membrane and measure displacement of a position of light reflected from the membrane.

Applying pressure within the chamber 1 to cause bulging of the membrane 9 is not the only technique for deforming the membrane. In an alternative technique, the membrane 9 can be deformed by reducing the pressure within the chamber 1 relative to ambient pressure outside the chamber 1. Under these alternative conditions, measurement of membrane displacement involves measuring the magnitude of indentation of the membrane. Also, under these alternative conditions, it is not necessary to hold the mask blank to the securing plate electrostatically.

Therefore the invention accurate measurements of the stress of multiple membrane regions of a segmented mask blank, without causing membrane deformation or fracture.

Whereas the invention has been described in connection with a representative embodiment, it will be understood that the invention is not limited to that embodiment. On the contrary, the invention is intended to encompass all modifications, alternatives, and equivalents as may be included within the spirit and scope of the invention, as defined by the appended claims.

What is claimed is:

1. A method for measuring stress in membrane regions of a segmented mask blank defining multiple subfields each having a respective membrane region flanked by struts that separate the subfields from one another, the method comprising:

mounting the mask blank on a securing plate such that the struts contact the securing plate, the securing plate defining an array of through-holes, the array having a pitch substantially equal to the pitch of subfields of the mask blank, the mask blank being situated on the securing plate such that the through-holes are aligned with individual respective subfields of the mask blank;

applying a differential pressure across the respective membrane regions of subfields aligned with respective through-holes;

measuring respective displacements of the membrane regions to which the differential pressure is being applied; and from the respective displacements, determining respective values of membrane stress of the membrane regions based on a relationship between the pressure and magnitude of membrane displacement.

2. The method of claim 1, wherein the differential pressure causes bulging of the membrane regions.

3. The method of claim 1, wherein the differential pressure causes indentation of the membrane regions.

4. The method of claim 1, wherein the relationship is:

$$P \cdot [r^2/(d \cdot h)] = K_1 \cdot \sigma + K_2 \cdot [E/(1-\gamma)] \cdot (h/r)^2$$

wherein P is pressure applied to the membrane region, $\sigma$ is membrane stress, E is Young's modulus, $\gamma$ is Poisson's ratio, r is a transverse dimension of the membrane or multiple thereof, d is membrane thickness, h is membrane bulge, and $K_1$ and $K_2$ are constants determined according to membrane shape.

5. An apparatus for measuring stress in membrane regions of a segmented mask blank defining multiple subfields each having a respective membrane region flanked by struts that separate the subfields from one another, the apparatus comprising:

a securing plate defining an array of through-holes, the array having a pitch substantially equal to the pitch of subfields of the mask blank, the securing plate being configured for placing the mask blank thereon such that the struts contact the securing plate and the through-holes are aligned with individual respective subfields of the mask blank;

a power supply connected at least to the securing plate and configured to generate an electrostatic force sufficient to attract the mask blank to the securing plate;

a mechanism for applying a differential pressure across the respective membrane regions of subfields aligned with respective through-holes; and a device for measuring respective displacements of the membrane regions to which the differential pressure is being applied.

6. The apparatus of claim 5, wherein:

the mechanism for applying a differential pressure comprises a chamber and a device, connected to the pressurizing chamber, configured for creating a pressure inside the chamber relative to outside the chamber, the chamber defining an opening; and the securing plate extends across the opening.

7. The apparatus of claim 5, wherein the device for measuring respective displacements is selected from the group consisting of instruments that employ a stylus-type displacement gauge, instruments that observe the membrane using a microscope for determining changes in focal position of various loci (e.g., center versus periphery) on the membrane, instruments that irradiate a light onto the membrane and measure membrane displacement by measuring changes in interference fringes of light reflected from the membrane versus from a reference surface, and instruments that irradiate a light onto the membrane and measure displacement of a position of light reflected from the membrane.

8. An apparatus for measuring stress in membrane regions of a segmented mask blank defining multiple subfields each having a respective membrane region flanked by struts that separate the subfields from one another, the apparatus comprising:

a securing plate defining an array of through-holes, the array having a pitch substantially equal to the pitch of subfields of the mask blank, the securing plate being configured for placing the mask blank thereon such that the struts contact the securing plate and the through-holes are aligned with individual respective subfields of the mask blank;

means for holding the mask blank to the securing plate;

means for applying a differential pressure across the respective membrane regions of subfields aligned with respective through-holes; and means for measuring respective displacements of the membrane regions to which the differential pressure is being applied.

9. The apparatus of claim 8, further comprising means for measuring membrane stress based on a relationship between the pressure and corresponding membrane displacement.

* * * * *

UNITED STATES PATENT AND TRADEMARK OFFICE
CERTIFICATE OF CORRECTION

PATENT NO. : 6,637,273 B2
DATED : October 28, 2003
INVENTOR(S) : Masashi Okada

It is certified that error appears in the above-identified patent and that said Letters Patent is hereby corrected as shown below:

Column 5,
Line 65, "invention accurate measurements" should read -- invention achieves accurate measurements --.

Signed and Sealed this

Twenty-second Day of February, 2005

JON W. DUDAS
*Director of the United States Patent and Trademark Office*